United States Patent
Pascal et al.

(10) Patent No.: US 8,671,966 B2
(45) Date of Patent: *Mar. 18, 2014

(54) NEEDLELESS ACCESS PORT VALVES

(75) Inventors: Benjamin J. Pascal, Allentown, PA (US); Edwin L. Burnard, Pen Argyl, PA (US); Kevin Jenkins, New Philadelphia, PA (US); Steve Broadbent, Dover, OH (US)

(73) Assignee: B. Braun Medical Inc., Bethlehem, PA (US)

( * ) Notice: Subject to any disclaimer, the term of this patent is extended or adjusted under 35 U.S.C. 154(b) by 392 days.

This patent is subject to a terminal disclaimer.

(21) Appl. No.: 13/152,904

(22) Filed: Jun. 3, 2011
(Under 37 CFR 1.47)

(65) Prior Publication Data
US 2011/0230845 A1   Sep. 22, 2011

Related U.S. Application Data (63) Continuation of application No. 11/942,163, filed on Nov. 19, 2007, now Pat. No. 8,015,990.

(60) Provisional application No. 60/866,339, filed on Nov. 17, 2006.

(51) Int. Cl.
*F16K 31/122* (2006.01)
*B21K 1/20* (2006.01)

(52) U.S. Cl.
USPC ............... 137/15.18; 251/149.1; 251/324; 29/890.124

(58) Field of Classification Search
USPC ............ 137/15.18, 15.01; 251/149.1, 149.6, 251/324; 29/890.124, 890.12
See application file for complete search history.

(56) References Cited

U.S. PATENT DOCUMENTS

| | | |
|---|---|---|
| 4,603,152 A | 7/1986 | Laurin et al. |
| 5,049,139 A | 9/1991 | Gilchrist |
| 5,354,267 A | 10/1994 | Niermann et al. |
| 5,536,258 A | 7/1996 | Folden |
| 5,547,000 A | 8/1996 | Kemp et al. |
| 5,782,808 A | 7/1998 | Folden |
| 6,822,034 B2 | 11/2004 | Hanke et al. |
| 6,871,838 B2 | 3/2005 | Raines et al. |
| 6,890,662 B2 | 5/2005 | Yaginuma et al. |

(Continued)

OTHER PUBLICATIONS

International Search Report mailed Jun. 25, 2008 from related International Application No. PCT/US2007/085130, filed Nov. 19, 2007 (3 pages).

(Continued)

*Primary Examiner* — Kevin Lee
(74) *Attorney, Agent, or Firm* — Klein, O'Neil & Singh, LLP (57) ABSTRACT

Needleless access port valves are generally discussed herein with particular discussions extended to needleless access port valves having a pliant valve piston and/or plug that exudes silicone oil when stressed or squeezed while providing antimicrobial agents within and on the surface of the piston and/or plug. The pliant valve piston may have an integrally formed plug and one or more ports or a separately formed plug located inside a plastic housing. The plug cooperates with a nozzle on the inlet connector assembly to form a slip port or a Luer inlet, which can open when exerted by force to permit flow or closes when the force is removed.

22 Claims, 4 Drawing Sheets

(56) References Cited

U.S. PATENT DOCUMENTS

| | | |
|---|---|---|
| 7,029,617 B2 | 4/2006 | Nishimuro et al. |
| 7,184,825 B2 | 2/2007 | Leinsing et al. |
| 8,015,990 B2 * | 9/2011 | Pascal et al. ............... 137/15.18 |
| 2002/0133124 A1 | 9/2002 | Leinsing et al. |
| 2003/0199835 A1 | 10/2003 | Leinsing et al. |
| 2004/0195538 A1 | 10/2004 | Raines et al. |
| 2004/0234572 A1 | 11/2004 | Martinod et al. |
| 2007/0001335 A1 | 1/2007 | Lin et al. |

OTHER PUBLICATIONS

Written Opinion mailed Jun. 25, 2008 from related International Application No. PCT/US2007/085130, filed Nov. 19, 2007 (6 pages).
Notice of Allowance mailed May 24, 2011 from corresponding U.S. Appl. No. 11/942,163, filed Nov. 19, 2007.
Final Office Action mailed Mar. 16, 2011 from corresponding U.S. Appl. No. 11/942,163, filed Nov. 19, 2007.
Office Action mailed Sep. 28, 2010 from corresponding U.S. Appl. No. 11/942,163, filed Nov. 19, 2007.

\* cited by examiner

NEEDLELESS ACCESS PORT VALVES

CROSS-REFERENCE TO RELATED APPLICATIONS

This application is a continuation of application Ser. No. 11/942,163, filed Nov. 19, 2007, now U.S. Pat. No. 8,015,990, which claims the benefit of provisional application Ser. No. 60/866,339, filed Nov. 17, 2006; the contents of each of which are expressly incorporated herein by reference.

Needleless access port valves are generally discussed herein with particular discussions extended to needleless access port valves having a piston comprising antimicrobial properties.

BACKGROUND

Needleless access port valves are widely used in the medical industry for accessing an IV line and/or the internals of a patient or subject. Exemplary patents or publications that describe needleless access port valves are disclosed in Pub. Nos. 2002/0133124 A1 to Leinsing et al. Publication No. US 2007/0191786 A1 and U.S. Pat. No. 6,871,838, both to Raines et al. The contents of each of the foregoing references are expressly incorporated herein by reference as if set forth in full. Generally speaking, prior art valves utilize a valve housing in combination with a moveable internal plug or piston to control the flow of fluid through a valve. The plug or piston may be moved by a syringe or a medical implement to open the inlet of the valve for accessing the interior cavity of the valve. When a fluid is delivered through the valve, fluid flow typically flows around the outside of the plug or piston in the direction towards the outlet. Upon removal of the syringe or medical implement, the plug or piston returns to its original position, either un-aided or aided by a biasing means, such as a spring or a diaphragm.

In some prior art valves, when the syringe or medical implement pushes the plug or piston, the plug or piston is pierced by an internal piercing device, such as a spike. The spike typically incorporates one or more fluid channels for fluid flow flowing through the pierced piston and then through the fluid channels in the spike. In yet other prior art valves, a self-flushing or positive flush feature is incorporated to push residual fluids confined inside the interior cavity of the valve to flow out the outlet when the syringe or medical implement is removed.

Concerns with prior art valves include microbial colonization and sterilization. The former has to do with bacteria growth within the valve housing and the latter with the ability to clean the inlet of bacteria growth, such as wiping the inlet and/or the piston with a swab. Pub No. 2002/0133124 A1 to Leinsing et al., previously incorporated by reference, teaches the use of an antimicrobial agents, such as silver, silver oxide, or silver sulfadiazine, that "maybe included in the material forming the flex-tube piston or may be added to the outer surface of the piston as a coating" to minimize or eliminate bacteria growth. However, no information was provided on the effectiveness of the antimicrobial agents on bacterial growth when added as an admixture and cured within a piston. Nor was there information provided on how the antimicrobial agents kill the bacterium when the agents are cured or confined within the piston walls. Presumably, when cured within the piston, at most, only metals trapped along the outer surfaces of the piston are active agents.

SUMMARY

Aspects of the present invention include a method for making an injection port valve. The method comprising the steps of forming a piston assembly, wherein the piston assembly comprises a piston having a slit along a top surface a body section having an exterior surface, a seal surface, and a piston cavity, wherein the piston is made by mixing a two-part liquid silicone rubber material together to form the body section, and wherein the body section comprises a wall having a wall thickness that emits liquid silicone from within the wall to the exterior surface; installing the piston assembly into an interior cavity of a valve housing, the valve housing comprising a cylinder end and a valve seat; wherein the seal surface is seated against the valve seat; and wherein the two-part liquid silicone rubber further comprises a blend of colorant, carrier, and antimicrobial agents.

Another method provided herein includes a method for making a piston for use with a valve assembly, wherein the piston assembly comprises a piston having a body section having an exterior surface, a seal surface, a slit along an upper surface and extending radially to an exterior surface and axially, and a piston cavity. The piston is made by mixing a two-part liquid silicone rubber material together to form the body section, and wherein the body section comprises a wall having a wall thickness that emits liquid silicone from within the wall to the exterior surface; stressing the piston so that it exudes silicone oil; and wherein the two-part liquid silicone rubber further comprises a blend of colorant, carrier, and antimicrobial agents.

Yet another aspect of the present invention includes a piston for regulating flow from an inlet port and an outlet port of a valve assembly comprising a wall surface defining a cavity, an upper surface, a singularly formed neck section having a slit, and a singularly formed body section; the piston being made from a two-part silicone material mixed with a blend of colorant, carrier, and antimicrobial agents.

These and other features and advantages of the present invention will become appreciated as the same become better understood with reference to the specification, claims and appended drawings.

BRIEF DESCRIPTION OF THE DRAWINGS

The drawings appended herein include.

DETAILED DESCRIPTION

The detailed description set forth below in connection with the appended drawings is intended as a description of the presently preferred embodiments of needleless access port valves or backcheck valves (herein "valves") provided in accordance with aspects of the present invention and is not intended to represent the only forms in which the present invention may be constructed or utilized. The description sets forth the features and the steps for constructing and using the valves of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

Figure 1:
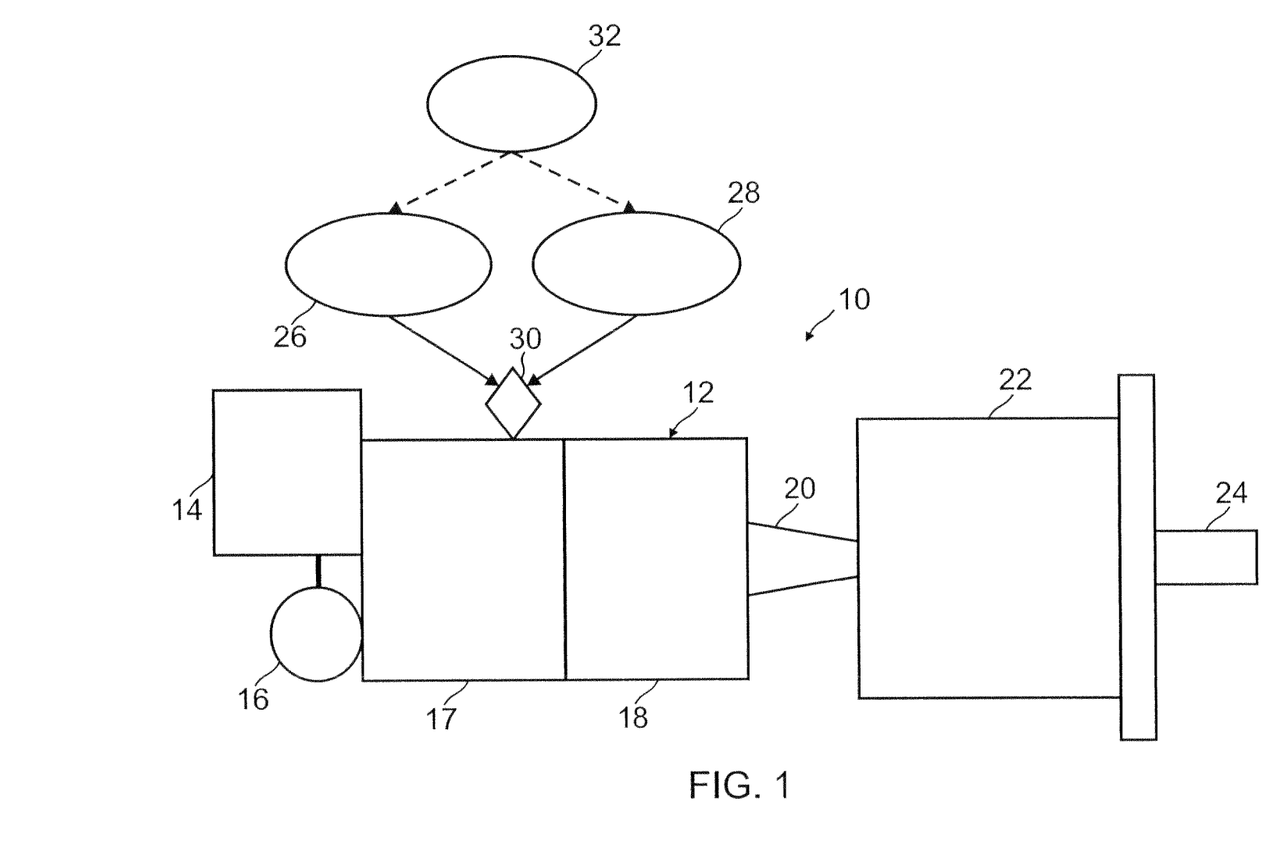
FIG. 1 is a schematic diagram of an injection molding machine for molding a flowable silicone rubber component provided in accordance with aspects of the present invention.

Referring now to FIG. 1, a system for manufacturing a piston having antimicrobial properties is shown, which is generally designated 10. The system 10 comprises an injection molding machine 12, which includes a hydraulic motor and gearing section 14, a hydraulic pump 16, a barrel 17 for receiving curable polymer or injectable material, and a pressure and heater chamber 18 for heating and compressing the injectable material. Heated and pressurized injectable material is then passed through a nozzle section 20 and then into a mold chamber 22, which comprises fixed and movable platens forming part of a clamping unit for the molds. Once shaped moldable elements, such as pistons or plugs, as further discussed below, are cured, they are discharged through the ejector 24.

As disclosed in the '838 patent and the '786 publication, both of which are to Raines et al., a silicone based piston for use in a housing valve may be made using the system 10 shown in FIG. 1 with a two-part flowable silicone system. The two-part system designed for liquid injection molding is available from Nusil Silicone Technology of Santa Barbara, Calif. When A and B components are mixed together, which are sold by Nusil Silicone Technology in a two-part kit, in equal portions, the liquid will cure to a tough, rubbery elastomer via addition-cure chemistry. After about sixty minutes of molding elapsed time, the cured silicone rubber will begin to self-lubricate a silicone fluid from within the wall surface of the piston to the piston exterior surfaces. The fluid flows from within the wall to the interior and exterior surfaces of the piston whenever the piston is stressed or squeezed, such as when the piston is compressed and released within the valve housing. As the piston exudes lubricant to the surfaces, the mass or density of the piston reduces approximately an equal amount.

Thus, stream A 26 may be fed into the barrel section 17 with stream B 28 in equal portions to form a preferred piston in accordance with aspects of the present invention. Preferably, a metering device or assembly 30, which may be external to or integrated with the molding machine 12, is used to meter the two streams in desired proportions. The fluid level or fluid flow to the surfaces can be adjusted with a formulation modification, such as by varying the ratio of component A and component B. Durometers available are 15, 30, 40, 50, 60 and 70 with a range of high and low level of bleed out for each of the durometer range. In one embodiment, the piston has the following physical properties: about 1.15 specific gravity with a range of about 1.1 to about 1.2 being acceptable; a 50 durometer Shore A with an acceptable range of about 40 to about 60 durometer; at least 600 psi minimum tensile strength with about 800 psi minimum being more preferred; an elongation rating of about 275% minimum with about 350% minimum being more preferred; and a tear strength of about 100 ppi (pounds per inch) minimum with 125 ppi being more preferred.

Part A of the two-part component includes a noble metal catalyst based on platinum, although palladium and rhodium may be also be used. Part B of the two-part component includes a silicone hydride-functional cross-linker, polydimethyl siloxane polymer, and internal lubricant, which is medical grade fluorosilicone fluid. The two-part system is pumped directly into the mixer of the barrel section 17 for homogenization and then directly into mold cavities located in the mold chamber 22. Vulcanization or curing occurs rapidly within the heated mold cavities, which is preferably maintained in the temperature range of about 245 to about 485 degrees F.

In accordance with one method of the present invention, antimicrobial metals in a third batch 32 may be added and combined with either stream A 26 or stream B 28 prior to introducing the two streams into the mixer 30. Exemplary antimicrobial metals include precious metals, such as silver, gold, platinum, copper, and zinc. Physiological antimicrobial metal compounds used herein include oxides and salts of preferably silver and also gold. These agents include silver acetate, silver benzoate, silver carbonate, silver citrate, silver chloride, silver iodide, silver nitrate, silver oxide, silver sulfadiazine, silver sulfate, gold chloride and gold oxide. Platinum compounds such as chloroplatinic acid or its salts (e.g., sodium and calcium chloroplatinate) may also be used. Alternatively, oxides and salts of copper and zinc such as those indicated above for silver may also be used. Preferred physiological antimicrobial metal compounds usable with the preferred piston of the present invention include silver acetate, silver oxide, ionic silver, silver sulfate, gold chloride, and a combination of silver oxide and gold chloride. In one exemplary embodiment, the agents are blended or mixed with stream A or stream B prior to combining the two streams in the mixer of the injection molding machine 12. The amount of antimicrobial agents is preferably in the range of 2% to 8% by wt/wt ratio of the combined stream. A colorant and a carrier, as further discussed below, may also be added with the antimicrobial agents into stream A or stream B.

Figure 2:
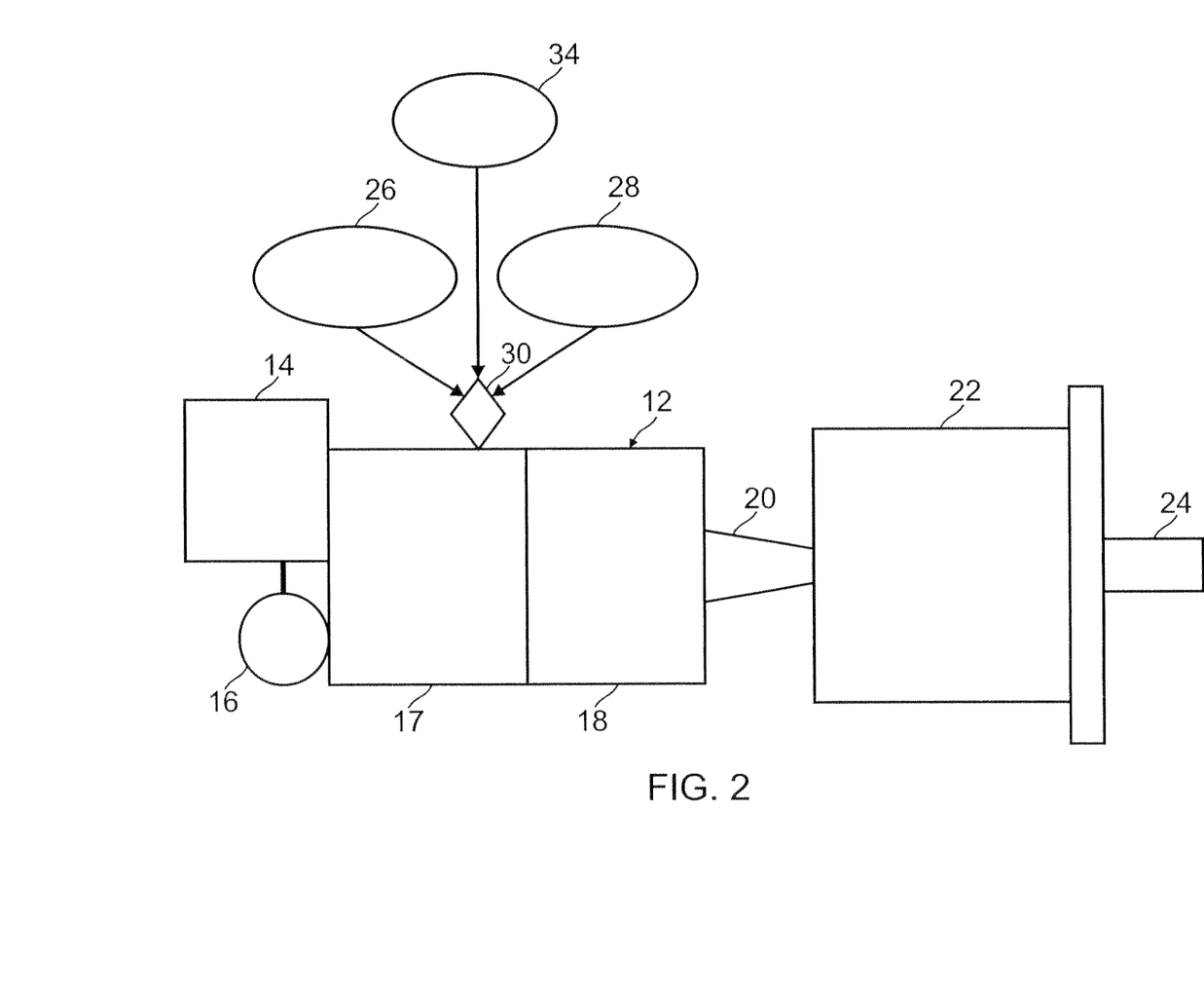
FIG. 2 is a an alternative schematic diagram of an injection molding machine for molding a flowable silicone rubber component provided in accordance with aspects of the present invention.

Although a piston for use in a valve assembly may be made in accordance with the method discussed above with reference to FIG. 1, in the preferred embodiment, the antimicrobial metals are blended with a colorant and a carrier prior to molding (i.e., pre-blended) and added to the two-part rubber compound as a third stream at the time of molding. With reference to FIG. 2, in the preferred alternative embodiment, three different streams 26, 28, 34 are combined simultaneously through three different feeds to form an admixture. An exemplary carrier usable with the blend of the present invention includes methylvinylpolysiloxane oil made by Shin-Etsu Chemical Co. LTD. An exemplary colorant includes phthalocyanine green pigment, described and supplied by Gayson Silicone Dispersions of Barberton. Ohio, as vinyl silicone elastomer/silica filler. The colorant/carrier/antimicrobial mix may be metered into the molding material at a ratio of about 3-14% by weight with 8% by weight of the total weight of a molded piston being more preferred. The mix 32, as noted above, is pre-blended as a third stream and contains about 60% antimicrobial metals by weight of the mix, with a range of 25% to 75% of the mix being permissible. The resultant piston has been found to effectively kill bacterium by exuding sufficient quantity of oil and antimicrobial agents from within the interior wall surfaces to the external surfaces of the piston to minimize or eliminate bacterium growth. A slow speed mixer or a static mixer may be used to pre-blend the third stream.

Figure 3:
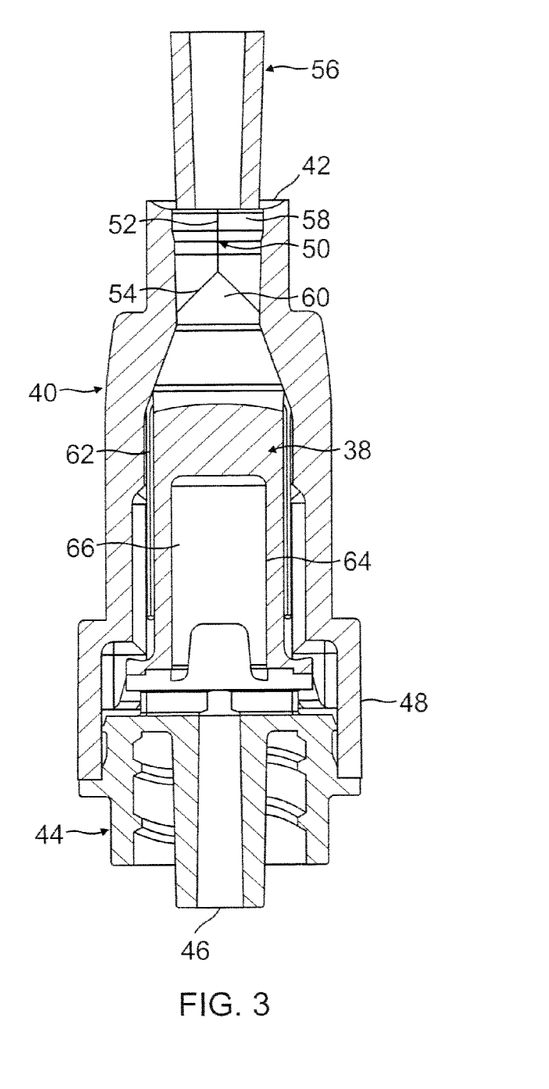
FIG. 3 is a cross-sectional side view of a needleless access port valve incorporating a piston made from a method of the present invention.

With reference now to FIG. 3, a cross-sectional side view a needleless access port valve 36 utilizing a piston 38 made in accordance with aspects of the present invention is shown. The valve 36 is similar to the valve shown in the '786 publication, which was previously incorporated by reference, and has a valve housing 40 having an inlet port 42 and a nut fitting 44, which comprises an outlet port 46, attached to a skirt section 48. The piston 38 is shown in a closed or less compressed position to terminate fluid flow between the inlet port 42 and the outlet port 46.

As disclosed in the '786 publication, the piston 38 comprises a slit 50, which comprises an upper slit section 52 and a lower slit section 54. When a medical implement 56, such as a syringe tip or a tubing connector, axially compresses the piston 38, a fluid pathway through the valve housing 40 is created as the piston neck section 52 is pushed against the actuator 60 to open a flow channel in the upper slit section 52 (See also FIG. 7). Fluid can now be introduced through the inlet port 42 and out the outlet port 46 or a sample may be taken in the reverse flow direction.

In one exemplary embodiment, the piston 38 is made in accordance with the method discussed with reference to FIG. 1 or FIG. 2. Thus, as the piston is compressed, squeezed, or otherwise stressed, liquid silicone and antimicrobial agents are exuded from within the wall surfaces of the piston and flow out to the outer 62 and inner exterior surfaces 64 of the piston cavity 66 to kill bacterium present in the valve.

Figure 4:
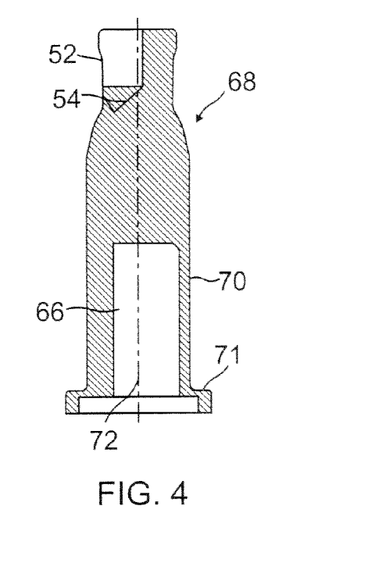
FIG. 4 is a cross-sectional side view of an alternative piston having a truncated bore for varying the thicknesses of the piston base section.
Figure 5:
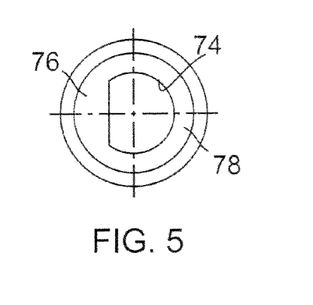
FIG. 5 is an end view of the piston of FIG. 4.

FIG. 4 is a cross-sectional side view of an alternative piston 68 provided in accordance with aspects of the present invention. The alternative piston 68 is similar to the piston 38 discussed with reference to FIG. 3 with the exception of the piston body 70 near the base section or flange 71. Whereas the wall thickness of the body section of the piston 38 in FIG. 3 is generally constant, the wall thickness of the alternative piston is not. In the embodiment shown, the wall thickness located directly below or distal of the slit 50 is thicker than the wall thickness located on the opposite side of the center plane 72. With reference to FIG. 5, which is an end view of the alternative piston 68, in one exemplary embodiment, the wall surface of the piston base section 70 is formed by molding a truncated cylindrical bore 74, which forms a thicker 76 base section and a relatively thinner base section 78. In other embodiment, the shape, thickness, and configuration can vary. In the embodiment shown, the thinner 78 wall section is configured compress a greater amount than the thicker section 76 whenever the piston 68 is acted on by a medical implement. This allows the piston 68 to cant or deflect unevenly, i.e., non-symmetrically, whenever compressed by a medical implement.

Figure 6:
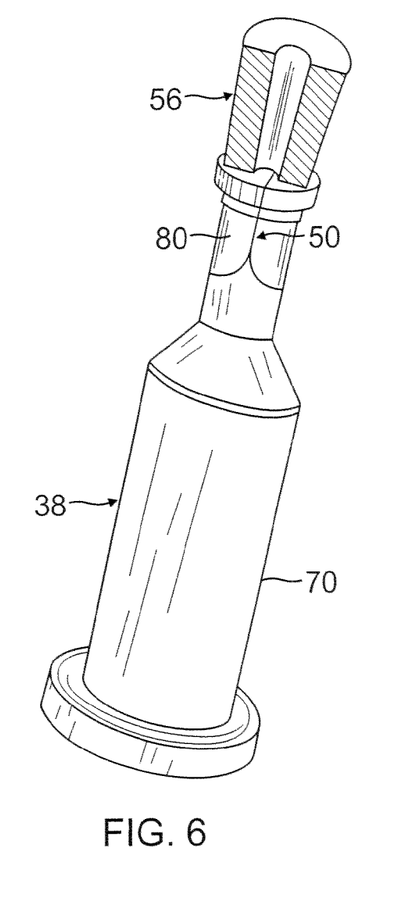
FIG. 6 is a clarified view of the piston of FIG. 3, shown without the housing for clarity.
Figure 7:
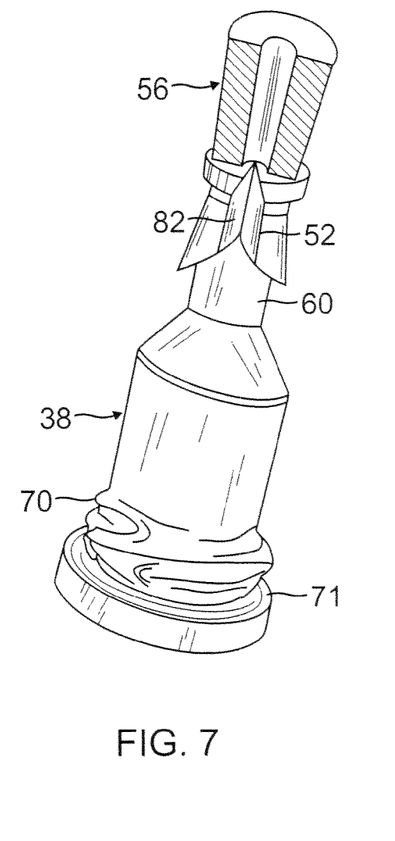
FIG. 7 shows the piston of FIG. 6 in a compressed state to expose a flow channel or gap.

FIGS. 6 and 7 are perspective views of the piston of FIG. 3 in a ready, less compressed, or uncompressed position (FIG. 6) and used or compressed position (FIG. 7), shown without the valve housing for clarity. In the ready position, the body section 70 recovers its generally cylindrical shape and pushes the upper neck section 80 into the inlet port and by action of the relative dimensions between the two, forces the slit 50 closed. However, when compressed by the medical implement 56, the body section 70 collapses into random folds and the upper neck section 80 abuts against the actuator 60 while it concurrently expands within the valve housing to expose a flow channel or gap 82 for fluid flow or sampling.

Although not shown, it is understood that when the alternative piston 68 is compressed, it resembles the piston shown in FIG. 7 with a few exceptions. In particular, the random folds are less pronounced along the thicker base section 76 than the thinner base section 78. Also, the piston slightly arches and bulges out near the thicker section due to the relative thicknesses of the piston body section. A metal spring may be incorporated in the interior cavity to assist the piston in returning to its less compressed state.

Although limited embodiments of the needleless access valve assemblies, their components, and preferred methods for making them from a flowable silicone-rubber-based material have been specifically described and illustrated herein, many modifications and variations will be apparent to those skilled in the art. For example, the various valves may incorporate luer-slips rather than luer threads, the material could be made opaque or semi-opaque, the various dimensions can vary, flow channels may be incorporated in the inlet lumen of the inlet connector assembly, etc. Furthermore, it is understood and contemplated that features specifically discussed for one valve embodiment may be adopted for inclusion with another valve embodiment, provided the functions are compatible. Accordingly, it is to be understood that the valve assemblies and their components constructed according to principles of this invention may be embodied other than as specifically described herein. The invention is also defined in the following claims.

What is claimed is:

1. A piston for regulating flow from an inlet port and an outlet port of a medical valve assembly comprising a wall surface defining a cavity, an upper surface, a singularly formed neck section having a slit, and a singularly formed body section; the piston being made from a first compound and a second compound forming a two-part silicone material mixed with a third compound comprising a blend of colorant, carrier, and antimicrobial agents; and the first compound, the second compound, and the third compound being a mixture of different feeds that are simultaneously mixed together to form an injectable material for molding the piston.

2. The piston of claim 1, wherein the slit extends radially to only one exterior surface of the neck section.

3. The piston of claim 1, wherein the slit is formed of an inverted Y-shape.

4. The piston of claim 1, further comprising a flange located distally of the body section.

5. The piston of claim 1, wherein the piston is located inside an interior cavity of a valve housing.

6. The piston of claim 1, wherein the antimicrobial agents comprise at least one of silver, gold, platinum, copper, zinc, oxides of any one of the agents, and salts of anyone of the agents.

7. A method for making a medical injection port valve comprising:

simultaneously mixing together a first compound from a first feed, a second compound from a second feed, and a third compound from a third feed to form an admixture;

foaming a piston comprising a slit along a top surface, a seal surface, a body section having an exterior surface, and a piston cavity, wherein the piston is made by admixture to form the body section;

installing the piston into an interior cavity of a valve housing having an inlet and an outlet; and wherein the first compound and the second compound form a two-part liquid silicone rubber compound and the third compound comprises a blend of a carrier and antimicrobial agents.

8. The method for making the medical injection port valve of claim 7, wherein the first compound, the second compound and the third compound are mixed together in a mixing chamber.

9. The method for making the medical injection port valve of claim 7, wherein the third compound further comprises a colorant.

10. The method for making the medical injection port valve of claim 9, wherein the colorant, carrier, and antimicrobial agents are blended to form the third compound prior to mixing with the first compound and the second compound.

11. The method for making the medical injection port valve of claim 7, wherein the antimicrobial agents comprise at least one of silver, gold, platinum, copper, zinc, oxides of anyone of the agents, and salts of any one of the agents.

12. The method for making the medical injection port valve of claim 9, wherein the antimicrobial agents make up about 2% to about 8% by wt/wt ratio of the blend of colorant, carrier, and antimicrobial agents.

13. The method for making the medical injection port valve of claim 7, wherein the piston has a durometer Shore A range of about 40 to about 60 durometer.

14. The method for making the medical injection port valve of claim 7, further comprising placing the piston inside a valve housing.

15. A system for making medical grade pistons for use with valve assemblies comprising:
  a mixing device for simultaneously mixing together at least a first compound, a second compound, and a third compound to form an admixture, each compound provided from a different feed, the first compound and the second compound forming a two-part silicon rubber compound;
  a pump for pumping the admixture;
  a pressure and heater chamber for heating and pressuring the admixture;
  a nozzle for discharging the admixture into a mold chamber, and
  wherein a plurality of pistons are formed, each piston comprising a body section having an exterior surface, a seal surface, and a piston cavity, and wherein the body section comprises a wall having a wall thickness that emits liquid silicone from within the wall to the exterior surface when stressed; and
  wherein the third compound comprises a blend of colorant, carrier, and antimicrobial agents.

16. The system of claim 15, wherein the blend of colorant, carrier, and antimicrobial of the third compound are mixed prior to combining with the first compound and the second compound.

17. The system of claim 15, wherein the colorant is phthalocyanine green pigment.

18. The system of claim 15, wherein the antimicrobial agents comprise at least one of silver, gold, platinum, copper, zinc, oxides of anyone of the agents, and salts of any one of the agents.

19. The system of claim 15, wherein the blend of colorant, carrier, and antimicrobial agents make up about 25% to about 75% of a total weight of the piston.

20. The system of claim 15, wherein the piston comprises a slit formed along an upper surface.

21. The system of claim 15, wherein the carrier comprises methylvinylpolysiloxane oil.

22. The system of claim 15, wherein one of the first compound or the second compound comprises a metal catalyst.

* * * * *

UNITED STATES PATENT AND TRADEMARK OFFICE
CERTIFICATE OF CORRECTION

| | | |
|---|---|---|
| PATENT NO. | : 8,671,966 B2 | Page 1 of 1 |
| APPLICATION NO. | : 13/152904 | |
| DATED | : March 18, 2014 | |
| INVENTOR(S) | : Benjamin J. Pascal et al. | |

It is certified that error appears in the above-identified patent and that said Letters Patent is hereby corrected as shown below:

On the title page, Item (73), in "Assignee", in column 1, line 1, Delete "Bethleham, PA" and insert -- Bethlehem, PA --, therefor.

On the title page, Item (74), in "Attorney, Agent, or Firm", in column 2, line 1, Delete "O'Neil" and insert -- O'Neill --, therefor.

In the Specification

In column 1, line 21, Delete "al." and insert -- al., --, therefor.

In column 2, line 45, Delete "a an" and insert -- an --, therefor.

In column 4, line 47, Delete "Barberton." and insert -- Barberton, --, therefor.

In the Claims

In column 6, line 45, in claim 7, Delete "foaming" and insert -- forming --, therefor.

Signed and Sealed this
Twelfth Day of August, 2014

Michelle K. Lee
*Deputy Director of the United States Patent and Trademark Office*